United States Patent
Reinsch et al.

(10) Patent No.: US 10,450,330 B2
(45) Date of Patent: Oct. 22, 2019

(54) PROCESS FOR PREPARING A ZIRCONIUM-BASED METAL ORGANIC FRAMEWORK

(71) Applicants: Universitetet I Oslo, Oslo (NO); Christian-Albrechts Universität zu Kiel, Kiel (DE); Katholieke Universiteit Leuven, Leuven (BE)

(72) Inventors: Helge Reinsch, Kiel (DE); Karl Peter Lillerud, Oslo (NO); Sachin Chavan, Lillestrøm (NO); Unni Olsbye, Oslo (NO); Dirk De Vos, Leuven (BE); Norbert Stock, Kiel (DE)

(73) Assignees: CHRISTIAN-ALBRECHTS UNIVERSITÄT ZU KIEL, Kiel (DE); KATHOLIEKE UNIVERSITEIT LEUVEN, Leuven (BE); UNIVERSITETET I OSLO, Blindern, Oslo (NO)

( * ) Notice: Subject to any disclaimer, the term of this patent is extended or adjusted under 35 U.S.C. 154(b) by 0 days.

(21) Appl. No.: 15/512,905

(22) PCT Filed: Sep. 25, 2015

(86) PCT No.: PCT/EP2015/072142
§ 371 (c)(1),
(2) Date: Mar. 21, 2017

(87) PCT Pub. No.: WO2016/046383
PCT Pub. Date: Mar. 31, 2016

(65) Prior Publication Data
US 2017/0291912 A1   Oct. 12, 2017

(30) Foreign Application Priority Data
Sep. 26, 2014   (GB) .................................. 1417076.5

(51) Int. Cl.
*C07F 7/00* (2006.01)
*C01G 25/04* (2006.01)
*C01G 25/06* (2006.01)
*C07C 63/26* (2006.01)

(52) U.S. Cl.
CPC .............. *C07F 7/00* (2013.01); *C01G 25/04* (2013.01); *C01G 25/06* (2013.01); *C07C 63/26* (2013.01); *C07F 7/003* (2013.01)

(58) Field of Classification Search
None
See application file for complete search history.

(56) References Cited

U.S. PATENT DOCUMENTS

| | | | |
|---|---|---|---|
| 5,466,846 A | 11/1995 | Sharif | |
| 7,411,081 B2 * | 8/2008 | Mueller | C07F 3/003 556/118 |
| 2009/0198079 A1 * | 8/2009 | Schubert | C07C 51/412 556/55 |

FOREIGN PATENT DOCUMENTS

WO   WO2009133366   * 11/2009 ............... C07F 7/00

OTHER PUBLICATIONS

Reinsch, Helg et al. "First examples of aliphatic zirconium MOFs and the influence of inorganic anions on their crytstal structures." Royal Society of Chemistry, CrystEngComm, 17, 2015, 331-337—publication date shown.*
Seetharaj et al. Arabian Journal of Chemistry (2019) 12, 295-315.*
Search Report dated Jul. 21, 2015 in connection with United Kingdom Patent Application No. 1417076.5, 4 pages.
International Search Report and Written Opinion dated Jan. 11, 2016 in connection with International Patent Application No. PCT/EP2015/072142, 12 pages.
Reinsch, Helge, et al. "First examples of aliphatic zirconium MOFs and the influence of inorganic anions on their crystal structures." Royal Society of Chemistry, CrystEngComm, 17, 2015, pp. 331-337.
Reinsch, Helge, et al. "Green synthesis of zirconium-MOFs." Royal Society of Chemistry, CrystEngComm, 17, 2015, pp. 4070-4074.
Yang, Qingyuan, et al. "A water stable metal-organic framework with optimal features for CO2 capture." Angewandte Communications, Angew. Chem. Int. Ed. 52, 2013, pp. 10316-10320.
Yang, Qingyuan, et al. "Supporting Information for a water stable metal-organic framework with optimal features for CO2 capture." Angewandte Chemi. Int. Ed., 2013, 19 pages.

* cited by examiner

*Primary Examiner* — Clinton A Brooks
(74) *Attorney, Agent, or Firm* — Dorsey & Whitney LLP

(57) ABSTRACT

There is provided a process for preparing a zirconium-based metal organic framework (Zr-MOF), the process comprising the steps (i) preparing a reaction mixture comprising zirconium ions, sulfate ions and at least one organic linker compound in an aqueous solvent; and (ii) heating the reaction mixture from step (i).

14 Claims, 3 Drawing Sheets

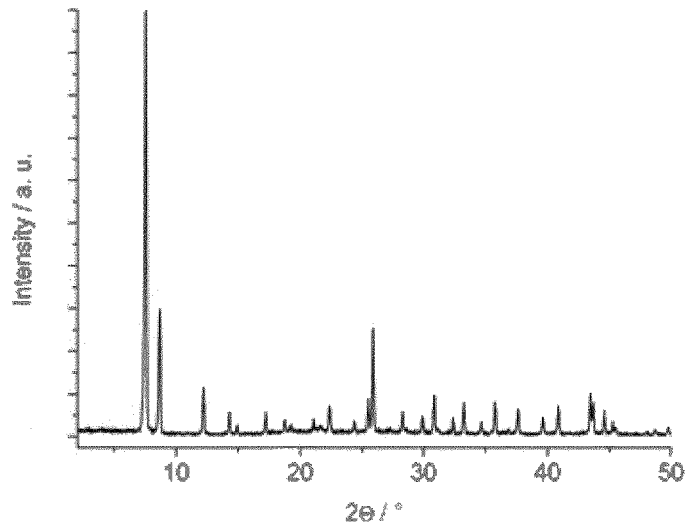
Figure 1: CuKα1 powder X-ray diffraction pattern of UiO-66(Zr)-COOH and UiO-66-2COOH produced by process of the invention.
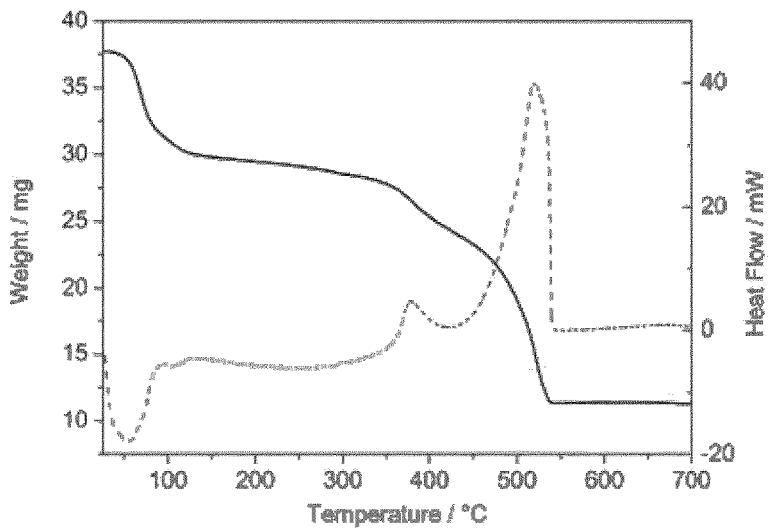
Figure 2: TG/DSC curves for UiO-66(Zr)-COOH produced by process of the invention, showing the weight loss (solid line) and energy connected to combustion of the material (dashed line) upon heating under a flow of nitrogen.

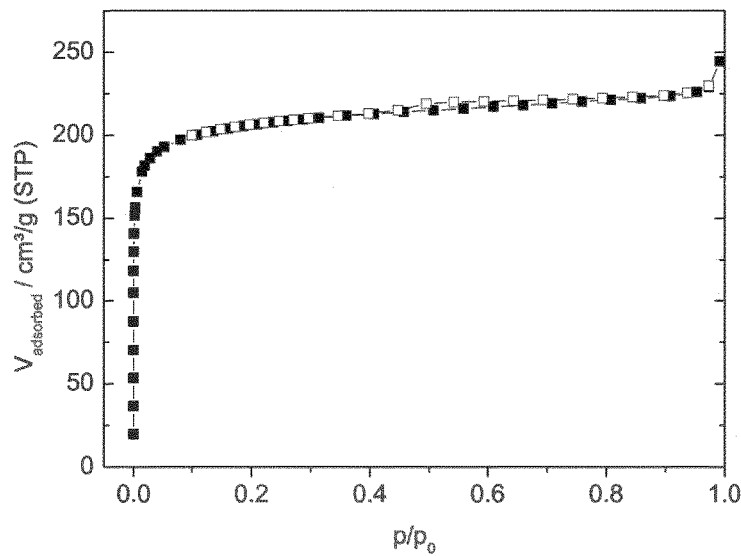
Figure 3: Adsorption isotherms measured with $N_2$ on UiO-66(Zr)-COOH at 77 K produced by the process of the invention. Filled symbols show the adsorption, empty symbols the desorption branch of the isotherm.
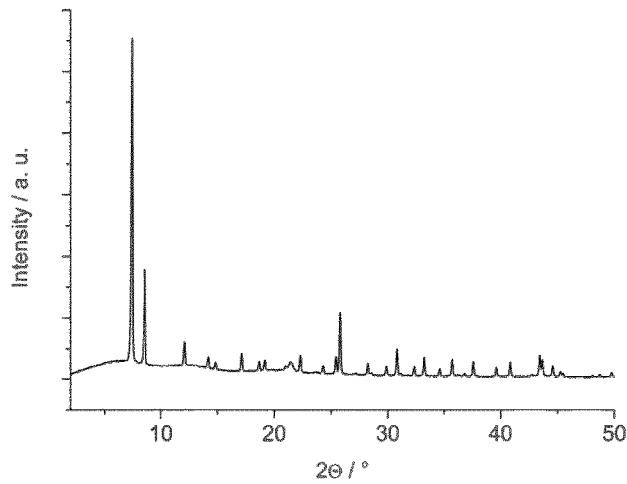
Figure 4: $CuK_{\alpha 1}$ powder X-ray diffraction pattern of UiO-66(Zr)-COOH produced by process of the invention after thermal activation and physisorption measurement.

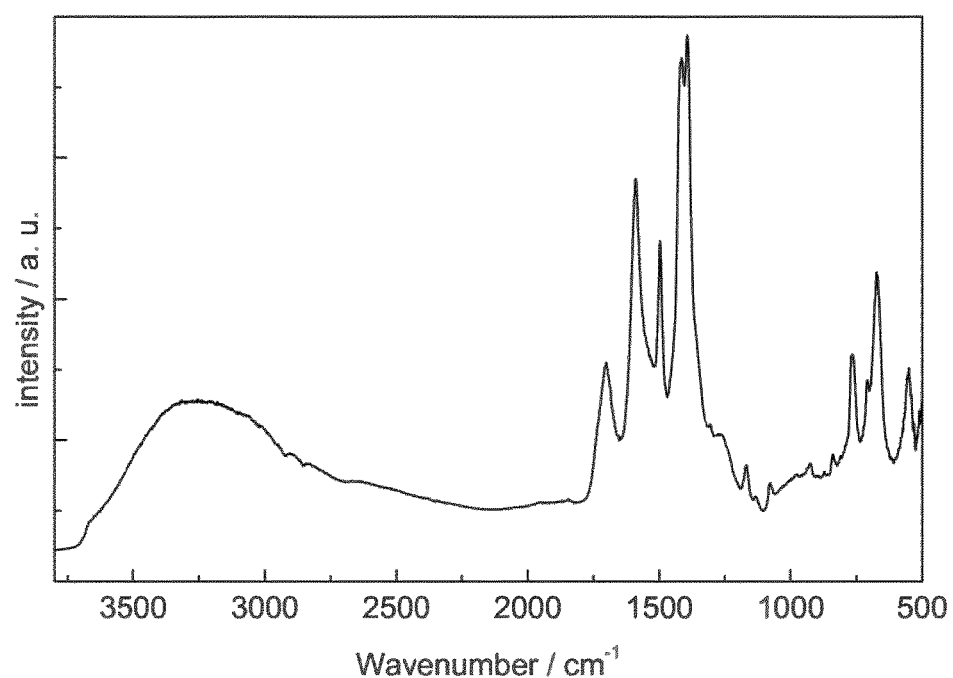
Figure 5: DRIFT spectrum of UiO-66(Zr)-COOH produced by process of the invention measured by the KBr pellet method.

PROCESS FOR PREPARING A ZIRCONIUM-BASED METAL ORGANIC FRAMEWORK

CROSS-REFERENCE TO RELATED APPLICATIONS

This application is a National Stage Application of International Patent Application No. PCT/EP2015/072142, filed Sep. 25, 2015, which claims priority to United Kingdom Application No. GB 1417076.5, filed Sep. 26, 2014, each of which is incorporated by reference herein, in the entirety and for all purposes.

FIELD OF THE INVENTION

The present invention relates to a process for preparing metal organic frameworks (MOFs), in particular to a process for preparing Zr-MOFs. The invention also relates to Zr-MOFs produced by such processes.

BACKGROUND

MOFs or "metal organic frameworks" are compounds having a lattice structure having vertices or "cornerstones" which are metal-based inorganic groups, for example metal oxides, linked together by organic linkers. The linkers are usually at least bidentate ligands which coordinate to the metal-based inorganic groups via functional groups such as carboxylate and/or amine. The porous nature of MOFs renders them promising materials for many applications such as gas storage and catalyst materials.

Perhaps the best known MOF is MOF-5 in which each $Zn_4O$ cornerstone is coordinated by six bis-carboxylate organic linkers. Other MOFs in which the inorganic cornerstone is for example chromium, copper, vanadium, cadmium or iron are also known. The processes of the present invention are directed specifically to zirconium-based MOFs (Zr-MOFs).

Numerous processes are known in the prior art for the production of MOFs. The most commonly used techniques involve the reaction of a metal salt with the desired organic linker in a suitable solvent, usually organic, such as dimethylformamide (DMF). High pressures and temperatures are commonly required to facilitate the reaction. Typical methods are disclosed in, for example, WO 2009/133366, WO 2007/023134, WO2007/090809 and WO 2007/118841.

The use of elevated temperatures and pressures not only increases the cost of the process but also means that scale-up to an industrial level poses many challenges. Apparatus suitable for withstanding the severe reaction conditions is often only compatible with small scale batch synthesis, rather than the continuous processes favoured for large scale production. Employing high pressures also carries with it safety concerns, particularly when combined with the use of corrosive liquids. Moreover, the use of organic solvents as the reaction medium is undesirable as such solvents are harmful to the environment and are expensive.

As MOFs become increasingly employed as alternatives to, for example, zeolites, there is a need for the development of novel processes for their production which are applicable to use on an industrial scale. Replacement of the organic solvent with an aqueous medium is reported in, for example, U.S. Pat. Nos. 7,411,081 and 8,524,932. These processes routinely involve the use of a base or require an alkaline reaction medium.

Moreover, reactions conditions which are suitable for the production of certain MOFs may not be transferable to others where different metals are used. For example, conditions found to be optimal for the production of MOFs containing main group metals from the second or third groups of the periodic table (e.g. magnesium or aluminium) are often not appropriate for the preparation of analogous frameworks wherein a transition metal is used.

The present invention is directed specifically towards Zr-MOFs. An aqueous-based process for producing a Zr-MOF is reported by Yang et al in Angew. Chem. Int. Ed. 2013, 52, 10316-10320. This process involves a two-step synthesis. The product is obtained as a gel which, to be isolated, must be washed and recrystallised. This adds to the costs and timescale of the process, making it unsuitable for use on a larger industrial scale.

There thus remains the need for the development of novel processes for the production of Zr-MOFs which are suitable for use on an industrial scale. The process should ideally be one which is "green" and thus considered environmentally friendly. It would also be advantageous to have a process which can be carried out quickly and cheaply and which offers improvements in terms of complexity over those processes already known in the art. In particular, a process which involves fewer steps is desired. A process which avoids potential corrosion problems, such as the production of hydrochloric acid (HCl) as a by-product is particularly attractive. A process susceptible to use in continuous production methods would also be advantageous. Ideally, a process which offers improvement in more than one of the above aspects would be developed.

The present inventors have surprisingly found that Zr-MOFs may be prepared in a straightforward process utilising an aqueous solvent which avoids the need for high temperatures and pressures. In particular, the specific combination of zirconium ions with sulfate ions in the reaction mixture unexpectedly leads to a procedure which is applicable to use on an industrial scale and offers an environmentally friendly and cheap route to these valuable materials.

SUMMARY OF THE INVENTION

Thus, in a first aspect, the invention provides a process for preparing a zirconium-based metal organic framework (Zr-MOF), comprising the steps:
(i) preparing a reaction mixture comprising zirconium ions, sulfate ions and at least one organic linker compound in an aqueous solvent; and
(ii) heating the reaction mixture from step (i).

In a further aspect, the invention provides a zirconium-based metal organic framework (Zr-MOF) produced or formable by the processes as herein described.

DETAILED DESCRIPTION

The present invention describes a process for the preparation of a zirconium-based metal organic framework (Zr-MOF). The process involves preparing a reaction mixture comprising zirconium ions, sulfate ions and at least one organic linker compound in an aqueous solvent and heating the reaction mixture. The process typically involves subsequently isolating the Zr-MOF.

Zr-MOF

As used herein, the term "Zr-MOF" is intended to cover any metal organic frameworks (MOFs) which comprise at least one zirconium metal ion. The Zr-MOFs of the invention have "cornerstones" which are zirconium inorganic groups. Typical zirconium inorganic groups include zirconium ions connected by bridging oxygen or hydroxide groups. These inorganic groups are further coordinated to at least one organic linker compound. In some cases, the inorganic groups may be further connected to non-bridging modulator species, complexing reagents or ligands (e.g. sulfates or carboxylates such as formate, benzoate or acetate) and/or solvent molecules. The zirconium oxide unit is usually based on an idealized octahedron of Zr-ions which are µ3-bridged by $O^{2-}$ and/or $OH^-$ ions via the faces of the octahedron and further saturated by coordinating moieties containing O-atoms like carboxylate groups. The idealised Zr oxide cluster is considered to be a $Zr_6O_{32}$-cluster which comprises between 6 and 12 (preferentially as close as possible to 12) carboxylate groups. However, in practice, there is a degree of flexibility in the structure of the cluster. The cluster may be represented by the formula $Zr_6O_x(OH)_{8-x}$ wherein x is in the range 0 to 8. For example, the cluster may be represented by the formula $Zr_6(O)_4(OH)_4$, Zr-MOFs are well known in the art and cover structures in which the zirconium cornerstone is linked to an at least bidentate organic linker compound to form a coordinated network. The structures may be one- two- or three-dimensional. The Zr-MOF usually comprises pores which are present in the voids between the coordinated network of zirconium ions and organic linker compounds. The pores are typically micropores, having a diameter of 2 nm or less, or mesopores, having a diameter of 2 to 50 nm.

Whilst it not outside the bounds of the present invention for the Zr-MOF to comprise additional metal ions other than zirconium, such as hafnium, titanium, or cerium, zirconium may be the only metal ion present. If additional metal ions are present these may be present in an amount of up 50 wt % relative to total amount of metal ions, preferably up to 25 wt %, more preferably up to 10 wt %, e.g. up to 5 wt %.

The Zr-MOFs of the invention particularly preferably have cornerstones having at least 12 coordination sites for the organic linkers, e.g. 12-36, especially preferably at least 14, 16 or 18, most especially 24. In this way at least 6, more preferably at least 8, especially at least 12 bidentate ligand groups of the organic linkers can bind to each cornerstone.

In all embodiments, the surface area of the Zr-MOF is preferably at least 400 m$^2$/g, more preferably at least 500 m$^2$/g, especially at least 700 m$^2$/g, such as at least 1020 m$^2$/g, for example at least 1050 m$^2$/g, e.g. at least 1200 m$^2$/g. The surface area may be up to 10000 m$^2$/g, especially up to 5000 m$^2$/g. It will be understood that, where functionalised organic linker compounds are used, the presence of additional, and often bulky, groups may affect (i.e. reduce) the surface area of the Zr-MOF.

In addition to the inorganic zirconium "cornerstones", the Zr-MOFs of the invention comprise at least one organic linker compound. The organic linker compound is at least bidentate, i.e. has at least two functional groups capable of coordinating to the zirconium cornerstones. The organic linker compound may also be tridentate (i.e. containing three functional groups) or tetradentate (i.e. containing four functional groups).

The Zr-MOF may have a Zr metal ion to organic linker molecule ratio of from 1:0.45 to 1:0.55, especially 1:0.49 to 1:0.51, particularly 1:0.5. Other preferred Zr metal ion to organic linker molecule ratios are 0.5:1, 1:1, 3:1 and 1:3, especially 1.1.

The organic linker compounds of the Zr-MOFs of the invention may be any organic linker molecule or molecule combination capable of binding to at least two inorganic cornerstones and comprising an organic moiety. By "organic" moiety we mean a carbon based group which comprises at least one C—H bond and which may optionally comprise one or more heteroatoms such as N, O, S, B, P, Si. Typically, the organic moiety will contain 1 to 50 carbon atoms.

The organic linker compound may be any of the linkers conventionally used in MOF production. These are generally compounds with at least two cornerstone binding groups, e.g. carboxylates, optionally with extra functional groups which do not bind the cornerstones but may bind metal ions on other materials it is desired to load into the MOF. The introduction of such extra functionalities is known in the art and is described for example by Campbell in JACS 82:3126-3128 (1960).

The organic linker compound may be in the form of the compound itself or a salt thereof, e.g. a disodium 1,4-benzenedicarboxylate salt or a monosodium 2-sulfoterephthalate salt.

The organic linker compound is preferably water soluble. By water soluble we mean that it preferably has a solubility in water which is high enough to enable the formation of a homogenous solution in water. The solubility of the organic linker compound in water may be at least 1 g/L at room temperature and pressure (RTP), preferably at least 2 g/L, more preferably at least 5 g/L.

The organic linker compound comprises at least two functional groups capable of binding to the inorganic cornerstone. By "binding" we mean linking to the inorganic cornerstone by donation of electrons (e.g. an electron pair) from the linker to the cornerstone. Preferably, the linker comprises two, three or four functional groups capable of such binding.

Typically, the organic linker comprises at least two functional groups selected from the group of carboxylate (COOH), amine (NH$_2$), nitro (NO$_2$), anhydride and hydroxyl (OH) or a mixture thereof. In a preferable embodiment, the linker comprises two, three or four carboxylate or anhydride groups, most preferably carboxylate groups.

The organic linker compound comprising said at least two functional groups may be based on a saturated or unsaturated aliphatic compound or an aromatic compound. Alternatively, the organic linker compound may contain both aromatic and aliphatic moieties.

In one embodiment, the aliphatic organic linker compound may comprise a linear or branched $C_{1-20}$ alkyl group or a $C_{3-12}$ cycloalkyl group. The term "alkyl" is intended to cover linear or branched alkyl groups such as all isomers of propyl, butyl, pentyl and hexyl. In all embodiments, the alkyl group is preferably linear. Particularly preferred cycloalkyl groups include cyclopentyl and cyclohexyl.

In a particularly preferred embodiment, the organic linker compound comprises an aromatic moiety. The aromatic moiety can have one or more aromatic rings, for example two, three, four or five rings, with the rings being able to be present separately from one another and/or at least two rings being able to be present in condensed form. The aromatic moiety particularly preferably has one, two or three rings, with one or two rings being particularly preferred, most preferably one ring. Each ring of said moiety can independently comprise at least one heteroatom such as N, O, S, B, P, Si, preferably N, O and/or S.

The aromatic moiety preferably comprises one or two aromatic C6 rings, with the two rings being present either separately or in condensed form. Particularly preferred aromatic moieties are benzene, naphthalene, biphenyl, bipyridyl and pyridyl, especially benzene.

Examples of suitable organic linker compounds include oxalic acid, ethyloxalic acid, fumaric acid, 1,3,5-benzene tribenzoic acid (BTB), benzene tribiphenylcarboxylic acid (BBC), 5,15-bis (4-carboxyphenyl) zinc (II) porphyrin (BCPP), 1,4-benzene dicarboxylic acid (BDC), 2-amino-1, 4-benzene dicarboxylic acid (R3-BDC or H2N BDC), 1,2, 4,5-benzene tetracarboxylic acid, 2-nitro-1,4-benzene dicarboxylic acid 1,1'-azo-diphenyl 4,4'-dicarboxylic acid, cyclobutyl-1,4-benzene dicarboxylic acid (R6-BDC), 1,2,4-benzene tricarboxylic acid, 2,6-naphthalene dicarboxylic acid (NDC), 1,1'-biphenyl 4,4'-dicarboxylic acid (BPDC), 2,2'-bipyridyl-5,5'-dicarboxylic acid, adamantane tetracaboxylic acid (ATC), adamantane dibenzoic acid (ADB), adamantane teracarboxylic acid (ATC), dihydroxy-terephthalic acid (DHBDC), biphenyltetracarboxylic acid (BPTC), tetrahydropyrene 2,7-dicarboxylic acid (HPDC), pyrene 2,7-dicarboxylic acid (PDC), pyrazine dicarboxylic acid, acetylene dicarboxylic acid (ADC), camphor dicarboxylic acid, fumaric acid, benzene tetracarboxylic acid, 1,4-bis(4-carboxyphenyl)butadiyne, nicotinic acid, and terphenyl dicarboxylic acid (TPDC). Other acids besides carboxylic acids, e.g. boronic acids may also be used. Anhydrides may also be used.

In a particularly preferred embodiment, the organic linker compound is selected from the group consisting of 1,4-benzene dicarboxylic acid (BDC), 2-amino-1,4-benzene dicarboxylic acid, 1,2,4-benzene tricarboxylic acid, 1,2,4,5-benzene tetracarboxylic acid and 2-nitro-1,4-benzene dicarboxylic acid or mixtures thereof.

A mixture of two or more of the above-mentioned linkers may be used. It is preferably, however, if only one type of linker is used.

The Zr-MOF is preferably of UiO-66 type. UiO-66 type Zr-MOFs cover structures in which the zirconium inorganic groups are $Zr_6(O)_4(OH)_4$ and the organic linker compound is 1,4-benzene dicarboxylic acid or a derivative thereof. Derivatives of 1,4-benzene dicarboxylic acid used in UiO-66 type Zr-MOFs include 2-amino-1,4-benzene dicarboxylic acid, 2-nitro-1,4-benzene dicarboxylic acid, 1,2,4-benzene tricarboxylic acid and 1,2,4,5-benzene tetracarboxylic acid.

When the linker is 1,4-benzene dicarboxylic acid, the resulting MOF may be referred to as UiO-66(Zr). When the linker is 2-amino-1,4-benzene dicarboxylic acid, the resulting MOF may be referred to as UiO-66(Zr)—$NH_2$. When the linker is 1,2,4-benzene tricarboxylic acid, the resulting MOF may be referred to as UiO-66(Zr)—COOH. When the linker is 1,2,4,5-benzene tetracarboxylic acid, the resulting MOF may be referred to as UiO-66(Zr)-2COOH.

A mixture of linkers may be used to introduce one or more functional groups within the pore space, e.g. by using aminobenzoic acid to provide free amine groups or by using a shorter linker such as oxalic acid. This introduction of functionalised linkers is facilitated by having a Zr-MOF with inorganic cornerstones with a high number of coordination sites. Where the number of these coordination sites exceed the number required to form the stable 3D MOF structure, functionalisation of the organic linkers may be effected, e.g. to carry catalytic sites, without seriously weakening the MOF structure.

By "functionalised MOF" we mean a MOF wherein one or more of the backbone atoms of the organic linkers carries a pendant functional group or itself forms a functional group. Functional groups are typically groups capable of reacting with compounds entering the MOF or acting as catalytic sites for reaction of compounds entering the MOF. Suitable functional groups will be apparent to a person skilled in the art and in preferred embodiments of the invention include amino, nitro, thiol, oxyacid, halo (e.g. chloro, bromo, fluoro) and cyano groups or heterocyclic groups (e.g. pyridine), each optionally linked by a linker group, such as carbonyl. The functional group may also be a phosphorus- or sulfur-containing acid.

A particularly preferred functional group is halo, most preferably a fluoro group.

Preferably, the functionalised Zr-MOF has a surface area of at least 400 $m^2/g$, more preferably at least 500 $m^2/g$, especially at least 700 $m^2/g$, such as at least 1020 $m^2/g$.

Process

The process of the invention comprises at least the steps of:

(i) preparing a reaction mixture comprising zirconium ions, sulfate ions and at least one organic linker compound in an aqueous solvent; and (ii) heating the reaction mixture from step (i).

The organic linker compound may be any organic linker as hereinbefore defined. It will be understood that the organic linker described in the context of the Zr-MOF produced by the processes of the invention is the same organic linker which is used as a starting material in step (i) of the process of the invention, albeit that once bound to the inorganic cornerstone the organic linker will be deprotonated. Thus all preferable embodiments defined above relating to the organic linker in the context of the Zr-MOF apply equally to this compound as a starting material.

The zirconium ions will typically be in the +4 oxidation state, i.e. $Zr^{4+}$ ions.

The zirconium ions may be provided in any conventional way, and thus any conventional source of zirconium ions may be used. However the zirconium ions will typically be provided in the form of at least one zirconium salt. Any zirconium salt may be used. Typical zirconium salts include zirconium acetate, zirconium acrylate, zirconium carboxylate, zirconium sulfate, zirconium hydroxide, zirconium nitrate, zirconium oxynitrate, zirconium oxide, zirconium oxychloride and zirconium chloride, or mixtures thereof.

Where a zirconium salt is used, the salt is usually water soluble, i.e. preferably having a solubility of at least 1 g/L at room temperature and pressure (RTP), preferably at least 2 g/L, more preferably at least 5 g/L.

In a preferable embodiment, the zirconium salt is selected from the group consisting of hydroxide, sulfate or mixtures thereof. Whilst the use of a mixture of two or more different salts is encompassed by the invention, it is preferable if one salt is used. Most preferably, the salt is zirconium hydroxide (e.g. $Zr(OH)_4$) or zirconium sulfate (e.g. $Zr(SO_4)_2$ or $Zr(SO_4)_2 \cdot 4H_2O$), especially zirconium sulfate.

The use of zirconium salts such as sulfate and hydroxide has cost advantages because these starting materials are relatively cheap to obtain. Moreover, these preferable salts are safer to handle than certain other common salts and do not lead to the production of highly corrosive hydrochloric acid as a side-product.

The sulfate ions may be provided in any conventional way, and thus any conventional source of sulfate ions may be used, typically sulphuric acid or at least one sulfate salt.

In one embodiment, the sulfate ions are provided in the form of sulfuric acid ($H_2SO_4$). In another embodiment, the sulfate ions are provided in the form of at least one sulfate salt, such as zirconium sulfate (e.g. $Zr(SO_4)_2$ or $Zr(SO_4)_2 \cdot 4H_2O$), cerium (IV) sulfate, or hafnium sulfate, preferably zirconium sulfate.

In yet a further embodiment, the sulfate ions are provided in the form of a mixture of sulfuric acid and at least one sulfate salt, such as a mixture of sulfuric acid and zirconium sulfate (e.g. $Zr(SO_4)_2$ or $Zr(SO_4)_2 \cdot 4H_2O$), In one particularly preferred embodiment, the zirconium ions and the sulfate ions are provided from the same source, i.e. zirconium sulfate (e.g. $Zr(SO_4)_2$ or $Zr(SO_4)_2 \cdot 4H_2O$).

In another preferred embodiment, the zirconium ions are provided in the form of zirconium hydroxide ($Zr(OH)_4$) and the sulfate ions are provided in the form of sulfuric acid ($H_2SO_4$).

The zirconium ions, sulfate ions and at least one organic linker are mixed in aqueous solvent, i.e. comprising water. In one embodiment, the aqueous solvent consists of water. The pH of the aqueous solvent is preferably acidic, i.e. having a pH less than 7, more preferably pH 0-5, such as pH 0-3.

The reaction mixture prepared in step (i) of the processes of the invention is typically prepared by mixing the various components together in the aqueous solvent. Mixing may be carried out by any known method in the art, e.g. mechanical stirring. The mixing is preferably carried out at room temperature, i.e. 18 to 30° C. Usually, step (i) is carried out at or around atmospheric pressure, i.e. 0.5 to 2 bar, especially 1 bar.

In step (ii) of the process, the reaction mixture prepared in step (i) is heated. Heating is usually carried out to a temperature at which the reaction mixture boils. Preferably, the temperature is increased to 50-120° C., more preferably 60-110° C., such as 80-100° C., e.g. 95° C. Usually, step (ii) is carried out at or around atmospheric pressure, i.e. 0.5 to 2 bar, especially 1 bar.

The reaction mixture is preferably heated for a period of time of at least 20 minutes, more preferably at least 30 minutes, even more preferably at least 50 minutes, i.e. at least 60 minutes. The reaction mixture is preferably heated for not more than 10 hours, more preferably not more than 5 hours, especially not more than 2 hours.

Step (ii) is generally carried out by heating the reaction mixture from step (i) under reflux at the temperature and for the time periods as hereinbefore defined. The skilled man will appreciate that heating under reflux is a routine procedure with which anyone working in the field of the invention would be familiar.

The method of heating may be by any known method in the art, such as heating in a conventional oven, a microwave oven or heating in an oil bath.

The mild reactions conditions used in the process of the invention offer numerous advantages over those of previous methods wherein organic solvents were used as the reaction medium. The processes may be carried out in open vessels without the need for high pressures, temperatures or reaction times. This offers improvements in terms of costs, safety and suitability for industrial scale-up.

Moreover, it has surprisingly been found that the specific combination of zirconium ions and sulfate ions in the reaction mixture enable the direct formation of the Zr-MOF as an easy-to-handle powder. Thus, the preparation process may take place over significantly shorter timescales compared to the methods of the prior art.

The molar ratio of total zirconium ions to total organic linker compound(s) present in the reaction mixture prepared in step (i) is typically 1:1, however in some embodiments an excess of the organic linker compound may be used. Thus, in some embodiments, the molar ratio of total zirconium ions to total organic linker compound(s) in the reaction mixture is in the range 1:1 to 1:5, such as 1:4.

It will be appreciated that the Zr-MOF product forms during step (ii) of the process.

The processes of the invention usually comprise a further step (iii) isolating the Zr-MOF.

Advantageously, the Zr-MOF is usually formed as a crystalline product which can be isolated quickly and simply by methods such as filtration, or centrifugation. This offers an improvement over some methods of the prior art which produce an amorphous or gel-like product which must be further recrystallized before it can be isolated. The processes of the present invention thus preferably eliminate the need for these additional steps.

The isolation step (iii) is typically carried out by filtration, but isolation may also be performed by processes such as centrifugation, solid-liquid separations or extraction. After isolation, the Zr-MOF is preferably obtained as a fine crystalline powder having crystal size of 0.1 to 100 µm, such as 10 to 50 µm.

In addition to steps (i), (ii) and (iii), the processes of the invention may comprise additional steps, such as drying and/or cooling. Typically, there will be a cooling step between steps (ii) and (iii). Cooling usually involves bringing the temperature of the reaction mixture back to room temperature, i.e. 18-30° C.

In all embodiments of the invention, it is preferred the process is carried out in the absence of a base.

In a further embodiment, the invention relates to a zirconium-based metal organic framework (Zr-MOF) produced or formable by the processes as herein described.

Applications

The Zr-MOF produced or formable by the processes of the present invention may be employed in any known application for such materials. Applications therefore include, but are not restricted to, electrode materials, drug reservoirs, catalyst materials, adsorbents and cooling media.

FIGURES

FIG. 1: $CuK_{\alpha 1}$ powder X-ray diffraction pattern of UiO-66(Zr)—COOH produced by process of the invention clearly identifying the product as analogue of the UiO-66 (Zr)-structure.

FIG. 2: TG/DSC curves for UiO-66(Zr)—COOH produced by process of the invention, showing the weight loss (solid line) and energy connected to combustion of the material (dashed line) upon heating under a flow of nitrogen. This illustrates the high thermal stability of the obtained material of ~300° C.

FIG. 3: Adsorption isotherms measured with $N_2$ on UiO-66-COOH at 77 K produced by the process of the invention. The shape of the isotherm clearly proves the microporous nature of the products. Filled symbols show the adsorption, empty symbols the desorption branch of the isotherm.

FIG. 4: $CuK_{\alpha 1}$ powder X-ray diffraction pattern of UiO-66(Zr)—COOH produced by process of the invention after thermal activation and physisorption measurement. The data clearly shows the retention of the UiO-66(Zr)-structure after thermal treatment and sorption measurement.

FIG. 5: DRIFT spectrum of UiO-66(Zr)—COOH produced by process of the invention.

EXAMPLES

Techniques

Surface Area Measurement

The specific surface area was determined by means of $N_2$ physisorption measured on a Belsorp-mini apparatus at 77 K. Prior to the measurement the sample was activated at 373 K under vacuum for 3 h to remove occluded water molecules. The surface area was calculated by the BET-method (DIN 66131) and the Langmuir method (DIN 66135).

X-Ray Crystallography

The crystal structure was investigated by means of powder X-ray diffraction under ambient conditions in Bragg-Brentano-geometry utilizing Cu—K$_{\alpha 1}$-radiation.

Stability

The thermal stability was investigated by means of thermogravimetry coupled with differential scanning calorimetry. Therefore the sample was heated up with a rate of 1 K/min under a flow of nitrogen gas, constantly monitoring weight loss and the resulting heat of combustion.

IR-Spectroscopy

In-situ Diffuse Reflectence Infrared Fourier transform spectra (DRIFT) were recorded on KBr mixed with UiO-66(Zr)—COOH produced by the process of invention. Spectra were recorded at a resolution of 2 cm$^{-1}$ on a Bruker Vertex 70 spectrophotometer equipped with DTGS (Deutarated triglycine sulfate) detector.

Synthesis

Synthesis in a Microwave Oven.

The starting materials 1,2,4-benzenetricarboxylic acid (3.36 g) and Zr(SO$_4$)$_2$.4H$_2$O (1.42 g) are mixed in 20 mL of water in a microwave-vial equipped with a magnetic stirring bar. The mixture is heated at 95° C. under stirring for 60 minutes. After cooling down to room temperature by compressed air the resulting white solid is separated by filtration, washed with 20 mL of water and dried for 12 h at 90° C. to yield 1.0 g of UiO-66(Zr)—COOH.

Synthesis in a Conventional Oven.

The starting materials 1,2,4-benzenetricaboxylic acid (6.72 g) and Zr(SO$_4$)$_2$.4H$_2$O (5.68 g) are mixed in 40 mL of water in a Teflon-lined steel autoclave equipped with a magnetic stirring bar. The mixture is heated at 95° C. under stirring for 60 minutes in an oven. After cooling down to room temperature the resulting white solid is separated by filtration, washed with 40 mL of water and dried for 12 h at 90° C. to yield 2.3 g of UiO-66(Zr)—COOH.

Synthesis in a Capped Bottle.

The starting materials 1,2,4-benzenetricaboxylic acid (4.2 g) and Zr(SO$_4$)$_2$.4H$_2$O (3.55 g) are mixed in 25 mL of water in a Pyrex-glass bottle with screw-cap equipped with a magnetic stirring bar. The mixture is heated at 95° C. under stirring for 60 minutes in an oil bath. After cooling down to room temperature the resulting white solid is separated by filtration, washed with 25 mL of water and dried for 12 h at 90° C. to yield 1.45 g of UiO-66(Zr)—COOH.

Synthesis in a Round Bottom Flask.

In a round bottom flask (50 ml volume) with a reflux condenser, 1 g of Zr(SO$_4$)$_2$.4H$_2$O was dissolved in 14 mL water while stirring. Once the clear solution is obtained 2.67 g of 1,2,4-benzenetricarboxylic acid was added under stirring. This reaction mixture was placed in Oil bath which was set at 98° C. and kept stirring for 90 min. The resulting white solid separated by filtration, washed with water and acetone and dried in air to yield 1.09 g of UiO-66(Zr)—COOH. The exemplary data shown in FIGS. 1-4 was measured on a sample obtained in this way. The PXRD-patterns unambiguously prove the UiO-66-framework structure. The thermal stability is ~300° C. under nitrogen. The apparent specific surface area according to the BET-method is 797 m$^2$/g, applying the Langmuir method the specific surface area is 914 m$^2$/g.

The invention claimed is:

1. A process for preparing a zirconium-based metal organic framework (Zr-MOF), comprising the steps:
   (i) preparing a reaction mixture comprising zirconium ions, sulfate ions and at least one organic linker compound in an aqueous solvent; and
   (ii) heating the reaction mixture from step (i),
   wherein said Zr-MOF comprises pores and wherein said aqueous solvent consists of water and wherein the process is carried out in the absence of a base.

2. A process as claimed in claim 1, further comprising step (iii) isolating the Zr-MOF, wherein step (iii) is carried out by filtration.

3. A process as claimed in claim 1, wherein the zirconium ions are provided in the form of at least one zirconium salt.

4. A process as claimed in claim 3, wherein said zirconium salt(s) is selected from the group consisting of zirconium acetate, zirconium acrylate, zirconium carboxylate, zirconium sulfate, zirconium hydroxide, zirconium nitrate, zirconium oxynitrate, zirconium oxide, zirconium oxychloride and zirconium chloride, or mixtures thereof.

5. A process as claimed in claim 3, wherein said zirconium salt(s) is selected from the group consisting of zirconium sulfate and zirconium hydroxide, or mixtures thereof.

6. A process as claimed in claim 1, wherein the sulfate ions are provided in the form of sulfuric acid or at least one sulfate salt (e.g. zirconium sulfate).

7. A process as claimed in claim 1, wherein both the zirconium and sulfate ions are provided in the form of zirconium sulfate.

8. A process as claimed in claim 1, wherein the at least one organic linker compound comprises at least two functional groups selected from the group consisting of carboxylate (COOH), amine (NH$_2$), anhydride and hydroxyl (OH) or a mixture thereof.

9. A process as claimed in claim 1, wherein the at least one organic linker compound comprises a linear or branched C$_{1-20}$ alkyl group, a C$_{3-12}$ cycloalkyl group and/or an aromatic moiety, preferably an aromatic moiety such as benzene, naphthalene, biphenyl, bipyridyl or pyridyl.

10. A process as claimed in claim 1, wherein the organic linker compound is selected from the group consisting of 1,4-benzene dicarboxylic acid (BDC), 2-amino-1,4-benzene dicarboxylic acid, 1,2,4-benzene tricarboxylic acid, 2-nitro-1,4-benzene dicarboxylic acid and 1,2,4,5-benzene tetracarboxylic acid, or mixtures thereof.

11. A process as claimed in claim 1, wherein in step (ii) of the process, the reaction mixture from step (i) is heated to a temperature in the range 50-120° C.

12. A process as claimed in claim 1, wherein step (ii) is performed for a time period of at least 20 minutes.

13. A process as claimed in claim 1, wherein the Zr-MOF is produced as a crystalline powder.

14. A zirconium-based metal organic framework (Zr-MOF) produced by the process as defined in claim 1.

* * * * *